United States Patent
Honkura et al.

(10) Patent No.: US 6,659,771 B2
(45) Date of Patent: Dec. 9, 2003

(54) DENTURE ATTACHMENT

(75) Inventors: Yoshinobu Honkura, Tokai (JP); Kazuo Arai, Tokai (JP)

(73) Assignee: Aichi Steel Corporation, Tokai (JP)

( * ) Notice: Subject to any disclaimer, the term of this patent is extended or adjusted under 35 U.S.C. 154(b) by 78 days.

(21) Appl. No.: 09/926,483

(22) PCT Filed: Mar. 8, 2001

(86) PCT No.: PCT/JP01/01839

§ 371 (c)(1), (2), (4) Date: Nov. 9, 2001

(87) PCT Pub. No.: WO01/66034

PCT Pub. Date: Sep. 13, 2001

(65) Prior Publication Data

US 2003/0059740 A1 Mar. 27, 2003

(30) Foreign Application Priority Data

Mar. 9, 2000 (JP) .......................................... 2000-71091
Feb. 7, 2001 (JP) .......................................... 2001-31398

(51) Int. Cl.⁷ ............................................. A61C 13/235
(52) U.S. Cl. ....................................................... 433/189
(58) Field of Search ................................ 433/189, 220, 433/221

(56) References Cited

U.S. PATENT DOCUMENTS 5,425,763 A * 6/1995 Stemmann .................. 433/189
5,678,998 A  10/1997 Honkura et al.
5,954,506 A  9/1999 Tanaka
6,299,450 B1 * 10/2001 Honkura et al. ............ 433/189

FOREIGN PATENT DOCUMENTS

| EP | 0347510 | * 6/1988 |
| JP | 8-317941 | 12/1996 |
| JP | 9-224959 | 9/1997 |
| JP | 10-127664 | 5/1998 |
| JP | 10-229992 | 9/1998 |
| JP | 2001-37781 | 2/2001 |

* cited by examiner

*Primary Examiner*—Todd E. Manahan
(74) *Attorney, Agent, or Firm*—Oblon, Spivak, McClelland, Maier & Neustadt, P.C.

(57) ABSTRACT

A dental attachment including a magnetic apparatus with magnetic attractive force, and a keeper that is attracted by the magnetic apparatus. The keeper has a convex shaped part with an attractive surface, and an end face provided around and protruding from the convex shaped part. The magnetic apparatus has a permanent magnet. The magnetic apparatus includes a magnetic assembly with an attractive surface and a non-magnetic guide ring made of non-magnetic material around the magnetic assembly. The non-magnetic guide ring has an end face. The non-magnetic guide ring and the attractive surface of the magnetic assembly form a concave part that receives the convex part of the keeper, and the end face of the keeper faces the end face of the non-magnetic guide ring.

10 Claims, 5 Drawing Sheets

DENTURE ATTACHMENT

TECHNICAL FIELD

The present invention relates to the dental attachment that fixes denture in the mouth using magnetic attraction.

BACKGROUND ART

The prior dental magnetic attachment using magnetic attraction is shown in, for example, laid-open Japanese patent number 8-317941. This dental magnetic attachment comprises a magnetic assembly, which exerts the magnetic attractive force of a permanent magnet, and a keeper made of soft magnetic material that is attracted by the magnetic assembly. This magnetic assembly has a planar attractive surface that attracts the keeper, while the keeper has a surface that is attracted to the attractive surface of the magnetic assembly.

Though the attractive force of the dental attachment is strong in the direction of attraction, it is weak in the direction parallel to the attractive face.

Therefore, upon an external force in the oral cavity, the magnetic apparatus usually shifts in the direction parallel to the attractive face. That is, the magnetic apparatus moves parallel to the keeper and slips out of place, forming a considerable gap.

This gap lowers the magnetic attractive force causing the denture to come off easily. And this gap, which never occurs with natural teeth, also gives an unnatural feeling when chewing, and makes chewing with the denture less comfortable.

As shown in FIG. 7, laid-open Japanese patent number 11-276505 discloses a dental attachment that has a concave part 50 in a portion of the circumference of yoke 5 made of soft magnetic material in the magnetic assembly 8, and a convex part 60 in a portion of the circumference of keeper 6 made of soft magnetic material.

This invention aims to prevent the slipping out of place of the magnetic apparatus as seen in prior dental attachments by using said convex and concave parts.

FIG. 8 shows the arrangement of this dental attachment in a denture. The keeper 6 is cast in the root cap R, and the root cap R is embedded in the tooth root S. The magnetic assembly 8 is embedded in the denture T.

However, in this invention shown in FIG. 7, if while fitting the denture, one of the concave parts 50 in a portion of the circumference of the yoke 5 which is attracted to one of the concave parts 60 in a portion of the circumference of the keeper 6 embedded in the tooth root S, the magnetic assembly will be fixed in an inclined state. This makes it difficult to fix the attachment parallel to the attractive surface. Therefore application of the denture is difficult. Furthermore, removal is also difficult because the two components are fixed mechanically.

Accordingly, the present invention aims to offer a dental magnetic attachment, which is easy to fix and prevents movement and the formation of a gap between the magnetic assembly and the keeper.

DISCLOSURE OF THE INVENTION

The present invention is the dental attachment, which has a magnetic apparatus that exerts magnetic attraction and a keeper that is attracted to said magnetic apparatus. Said keeper has a convex part with a surface that is attracted by said magnetic apparatus. Said magnetic apparatus has a magnetic assembly, which has a built-in permanent magnet and an attractive surface, and a non-magnetic guide ring made of non-magnetic material that is arranged on the lateral face around said magnetic assembly. Said non-magnetic guide ring and said attractive surface of said magnetic assembly form a concave part which fits to said convex part of said keeper.

The present invention, the dental attachment, would allow relative movement between a magnetic apparatus and the keeper only within the admitted range between the concave part of the magnetic apparatus and the convex part of the keeper.

Therefore, the present invention allows for very little slipping and very little gap in the direction of attraction and in the direction parallel to the attractive face. Furthermore, this invention has a non-magnetic guide ring of the magnetic apparatus, made of non-magnetic material, which does not form a magnetic circuit in the combined convex and concave parts, so no magnetic attractive force acts in the combined parts.

In addition, while fitting a denture, even if one part of the magnetic apparatus comes near the keeper first, no strong magnetic force acts, which solves the problem of the magnetic assembly being fixed to the attractive surface in an inclined state and not being able to fix the attractive surface parallel because one part is fixed first. Therefore, it is easy to fix and remove the denture.

Furthermore, at least one part of the lateral face of said convex part of said keeper and at least one part of the inner lateral face of said non-magnetic guide ring could have a tapered part that could fit with each other.

This makes it easier to fix and remove the denture.

Also, at least one part of the inner lateral face of said non-magnetic guide ring and at least one part of the lateral face of said convex part of said keeper could have a straight part, providing an amount of friction between the adjacent straight faces. In this case, holding force similar to force between a body and a cap in a tea-caddy can be obtained.

And, said magnetic assembly comprises a yoke that is formed of a magnet inserting part with a bottom and lateral part, the permanent magnetic that is inserted in the magnet inserting part of the yoke, soft-magnetic shield plate comprising at least a part of said attractive surface over said permanent magnet, non-magnetic seal ring made of non-magnetic material between said soft magnetic shield and said yoke. Said non-magnetic guide ring is welded together with said yoke. The distance between said permanent magnet and the welded part, where said yoke is welded with said non-magnetic guide ring, is preferable to be the same or more than the thickness of said bottom of said yoke.

In this case, a decrease in magnetic force due to said weld can be avoided and excellent attraction can be achieved.

BEST MODES FOR CARRYING OUT THE INVENTION

Furthermore, the admitted range of the gap between said keeper and non-magnetic guide ring is preferable to be 0.1~0.2 mm. The admitted range of the gap enables the stress concentration to the abutment tooth to be diffused because the energy generated is diffused as friction when outside forces cause a gap of said range.

Embodiment 1

(Structure of Embodiment 1)

Figure 1:
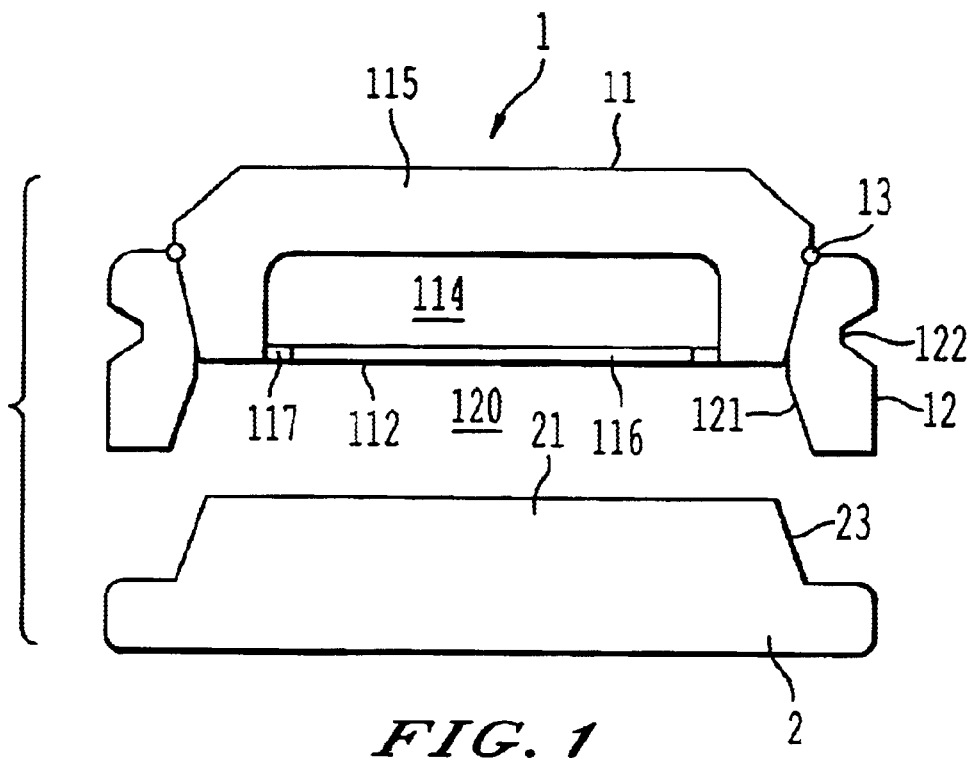
FIG. 1 is a cross section of the first embodiment of the dental magnetic attachment (separated condition).

In the invention according to the first embodiment, the dental magnetic attachment, as shown in FIG. 1, comprises a magnetic apparatus 1 and a keeper 2.

The magnetic apparatus 1 comprises a magnetic assembly 11 and a non-magnetic guide ring 12.

The magnetic assembly 11 and non-magnetic guide ring 12 are laser-welded at welding part 13. In the first embodiment, four places are welded. Welding at more than four places causes no problem. The first embodiment allows for any other ways to connect the two pieces.

The magnetic assembly 11 comprises a magnet 114, yoke 115, soft-magnetic shield plate 116, and non-magnetic seal ring 117. The inner face of yoke 115, and the gap between non-magnetic seal ring 117 and soft-magnetic shield plate 116 are sealed watertight. A rare-earth permanent magnetic such as Nd—Fe—B is used for the permanent magnet 114. 19Cr-2Mo soft-magnetic stainless steel is used for the yoke 115 and soft-magnetic shield plate 116. SUS316 equivalent is used for the nonmagnetic seal ring 117.

Non-magnetic guide ring 12 with magnetic assembly 11 makes concave part 120 of magnetic apparatus 1 to fit to convex part 21 of keeper 2.

At this time, the inner lateral face of non-magnetic guide ring 12 has taper 121.

Keeper 2 has a convex part 21 to fit the concave part 120 of said magnetic apparatus 1. The lateral face of convex part 21 of keeper 2 has taper 23.

Magnetic apparatus 1 and keeper 2 are fixed by the magnetic attractive force at the lower surface (attractive surface) 112 of magnetic assembly 11 and the upper surface 211 of convex part 21 of keeper 2.

Figure 2:
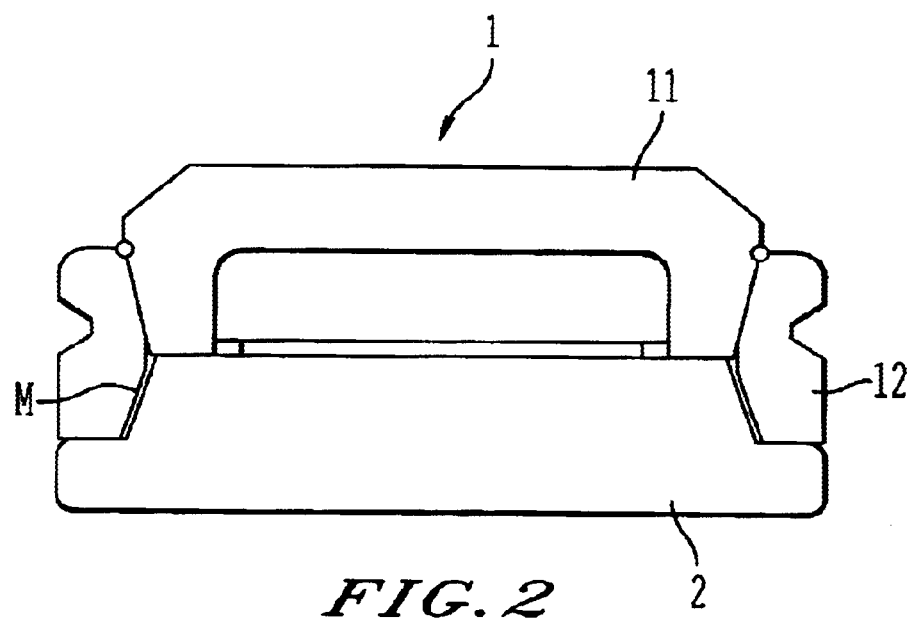
FIG. 2 is a cross section of the first embodiment of the dental magnetic attachment (attached condition).

As shown in FIG. 2, the admitted range of the gap M between the taper 121 of non-magnetic guide ring 12 and the taper 23 of keeper 2 is 0.2 mm at both sides.

The lateral face of non-magnetic guide ring 12 has a concave part 122 in its lateral face.

(Effect of the Embodiment)

This embodiment structured as mentioned above has the following effect.

Figure 3:
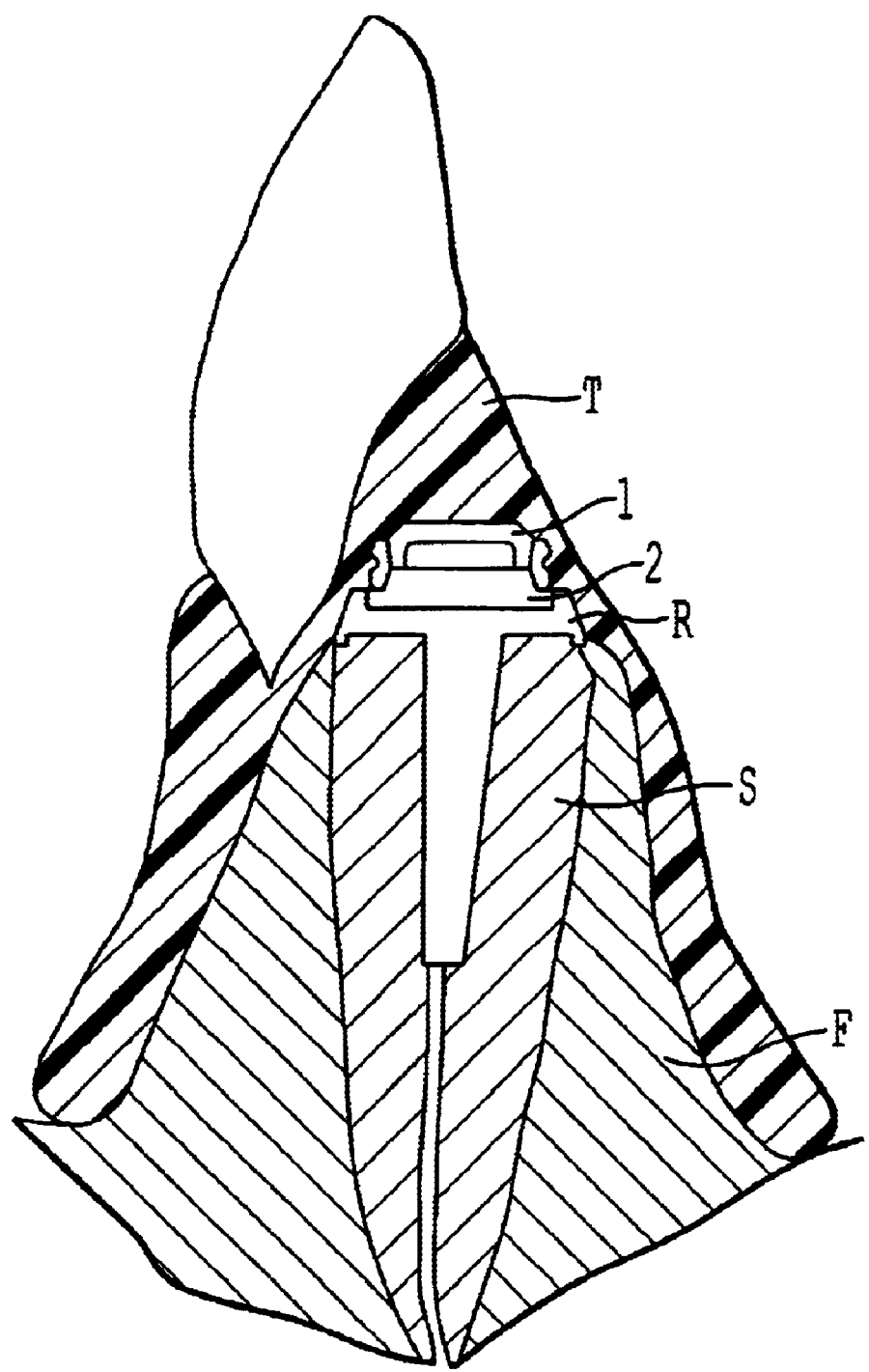
FIG. 3 is a cross section showing an installation of the first embodiment of the dental magnetic attachment.

As shown in FIG. 3, keeper 2 of present invention is cast in root cap R, and the root cap R is embedded in tooth root S. The magnetic apparatus 1 is embedded in denture T.

There are no inconveniences cased by magnetic apparatus 1, such as the denture falling off because of insufficient magnetic attraction due to a large gap.

The magnetic apparatus 1 is fixed to keeper 2, at the concave part 120 of said magnetic assembly 11 and the convex part 21 of keeper 2, and the admitted range of fitting gap M between them is 0.2 mm at both sides, which results in no relative movement in the attractive faces. Furthermore, if the admitted range of gap is 0.1 mm at both sides, better results can be seen.

With a gap of 0.2 mm or less, the denture has a natural feeling when chewing and is comfortable to wear.

Comfort is different for each individual, so in some cases, no problem occurs when the admitted range of fitting gap M is 0.1 mm in both sides. Less than 0.6 mm is preferable.

Furthermore, by having a non-magnetic guide ring 12 made of non-magnetic material as the part which is used to fit together magnetic apparatus 1 and keeper 2, even if one part of the magnetic apparatus 1 comes closer to the keeper 2 first, no strong attractive force acts, which solves the problem that it is difficult to fix the attachment to be parallel to the attractive surface because one part of the magnetic apparatus 1 is attached to the keeper 2 first and the magnetic assembly is fixed to the attractive surface in an inclined state. The work to fix and remove a denture becomes improved greatly.

In addition, having no convex and concave part in a part of the lateral face of a keeper or a part of the lateral face of a non-magnetic guide, the technical work to fix or remove the denture is easy, without the need for precise positioning.

However, when there is found to be large influence of rotation of the magnetic apparatus in the laboratory, an attachment with convex and concave parts in a portion of the lateral faces of the keeper and the non-magnetic guide can be used.

In addition, having a taper in the convex and concave parts in the non-magnetic guide ring 12 and keeper 2, the apparatus is fixed more smoothly.

By limiting the admitted range of the gap between the taper 121 of non-magnetic guide ring 12 and the taper 23 of keeper 2 to 0.2 mm at both sides, when said gap is caused by an outer force, the energy is dissipated by friction and the concentration of the force to the abutment tooth can be diffused. Furthermore, if the admitted range of gap can be limited to 0.1 mm at both sides, better results can be seen.

Forming a concave part in lateral face 122 of non-magnetic guide ring 12 prevents magnetic apparatus 1 from falling out of the denture base.

Embodiment 2

The second embodiment is an example of specific dimensions for same structure of magnetic apparatus 1 in embodiment 1.

Figure 4:
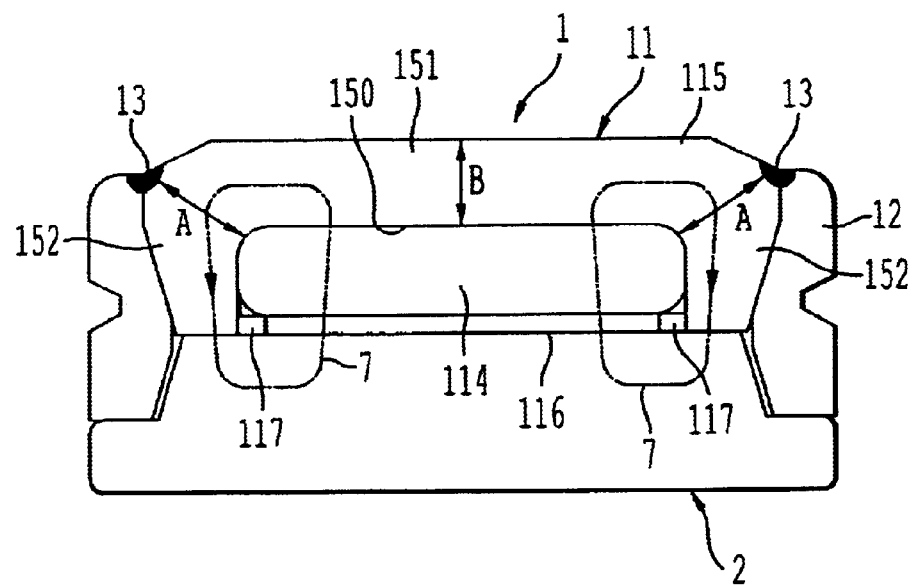
FIG. 4 is a cross section of the second embodiment of the dental magnetic attachment (attached condition).

As shown FIG. 4, the apparatus 1 of this example has a similar structure to that of example 1, comprising the yoke 115 that is formed of a magnet inserting part 150 with a bottom 151 and a lateral part 152, said permanent magnetic 114 that is inserted in magnet inserting part 150 of said yoke 115, a soft-magnetic shield plate 116 that consists at least of a part of said attractive part 112 over said permanent magnet 114, non-magnetic seal ring 117 made of non-magnetic material between said soft-magnetic shield plate 116 and said yoke.

Non-magnetic guide ring 12 is welded together to yoke 115. The distance A between welded part 13, between non-magnetic guide ring 12 and said yoke 115, and permanent magnet 114 is the same or narrower than the thickness B of the bottom 151 of yoke 115.

Because of these specific dimensions, in the present embodiment, when the magnetic circuit 7 that is produced surrounding non-magnetic seal ring 117 passes through yoke 115, sufficient volume of material is secured between said welding part 13 and permanent magnet 114 for the magnetic flux to be contained within the dental attachment. Therefore, it forms a very effective magnetic circuit and increases the magnetic attractive force.

Other effects are the same as those in embodiment 1.

Embodiment 3

In a third embodiment, the shape of non-magnetic guide ring 12 and keeper 2 in embodiment 1 are changed.

Figure 5:
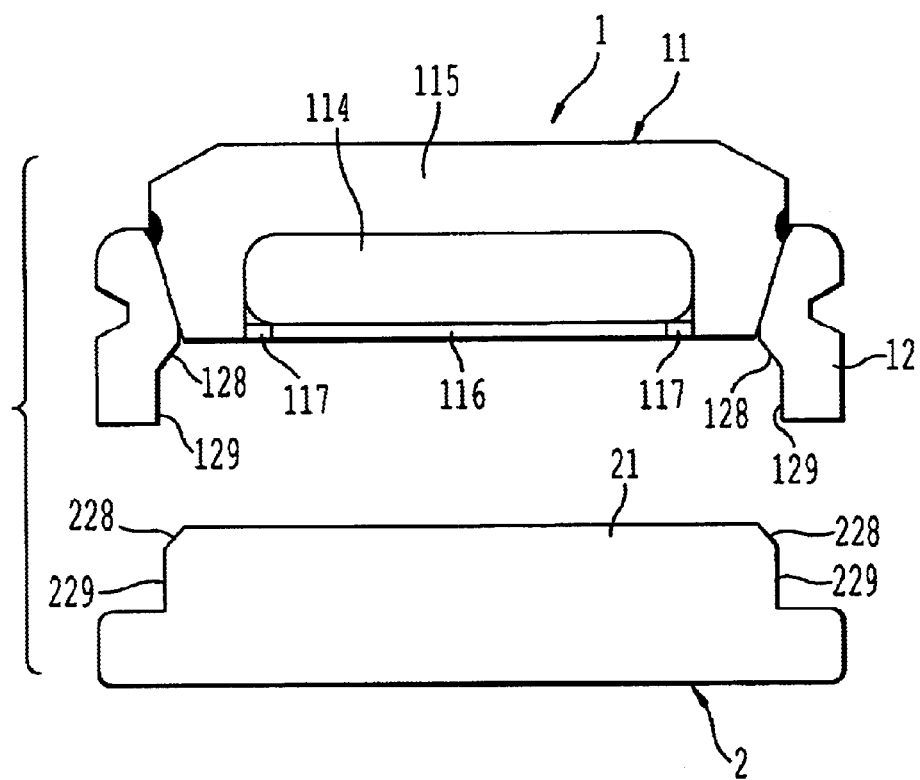
FIG. 5 is a cross section of the third embodiment of the dental magnetic attachment (attached condition).

Namely, as shown in FIG. 5, the lateral face of the convex part 21 of keeper 2 and the inner lateral part of the non-magnetic guide ring 12 have a tapered part 228 opposite to 128, and a straight part 229 opposite to 129. Other effects are the same as those in embodiment 1.

In this case, after magnetic apparatus 1 and keeper 2 are fit together, straight part 229 faces to 129, which makes it possible to get holding force similar to force between a body and a cap in a tea-caddy.

Other effects are the same as those in embodiment 1.

Embodiment 4

In a fourth embodiment, the structure and the shape of the magnetic apparatus 1 in embodiment 1 are changed.

Figure 6:
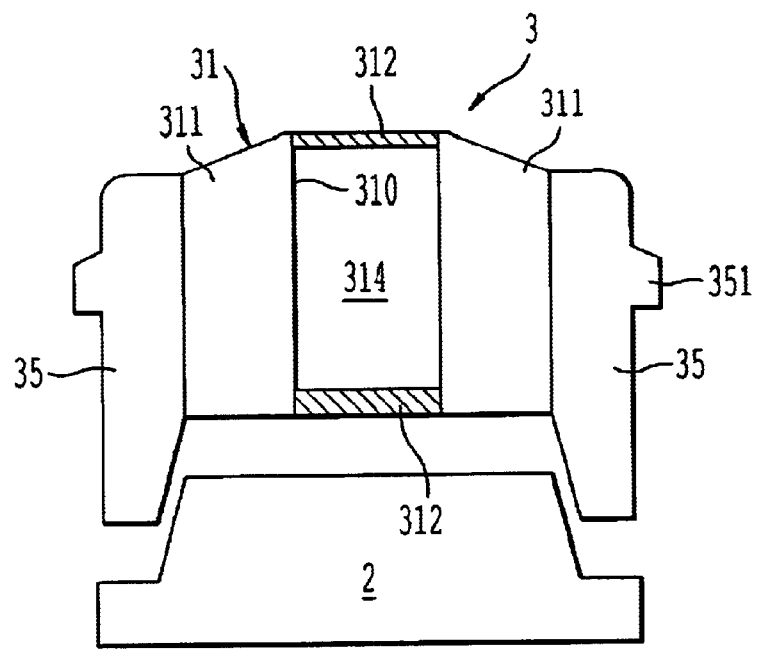
FIG. 6 is a cross section of the fourth embodiment of the dental magnetic attachment. (separated condition).
Figure 7:
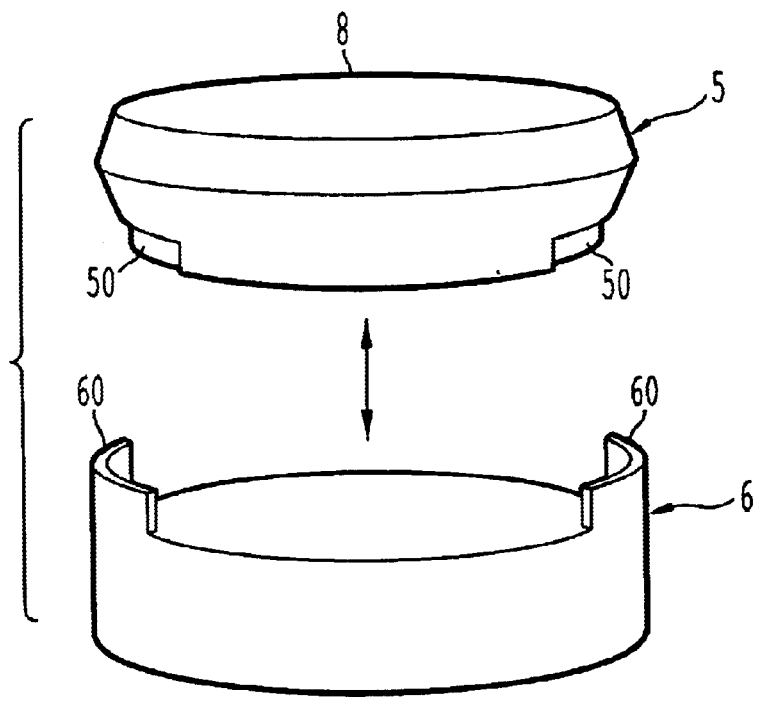
FIG. 7 is a perspective view of a prior example of the dental magnetic attachment.
Figure 8:
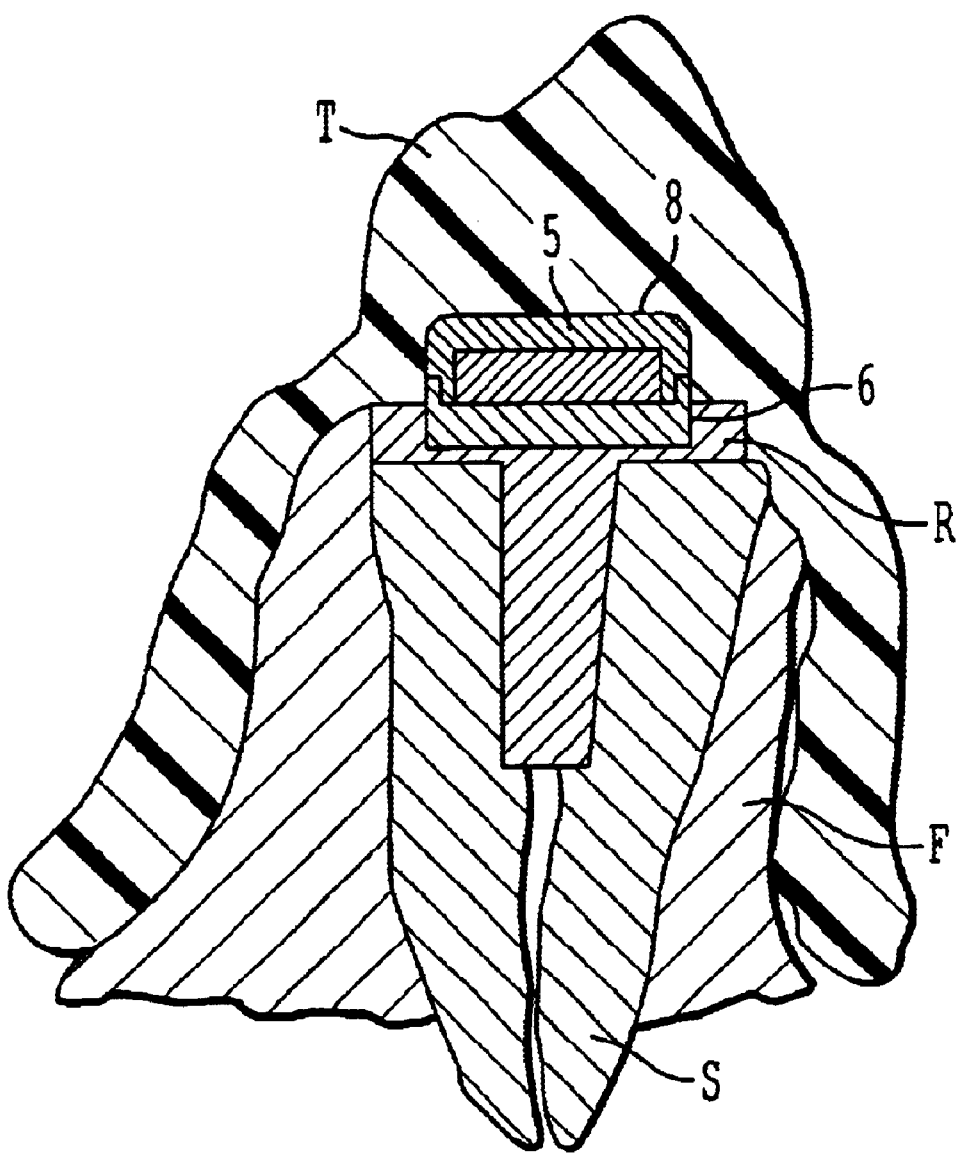
FIG. 8 is a cross section showing an installation of the prior example of dental magnetic attachment

Namely, as shown in FIG. 6, magnetic apparatus 3 of this embodiment has a sandwich-shaped magnetic assembly 31. Specifically, a permanent magnet 314, covered with non-magnetic cap 312, is sandwiched between yokes 311. The lateral face of yoke 311 is welded together with non-magnetic guide ring 35 made of non-magnetic material. The lateral face of yoke 311 is also welded together with the lateral face of non-magnetic cap 312. In addition, non-magnetic guide ring 35 has a projection 351.

Keeper 2 has the same structure as that in embodiment 1.

In this embodiment, other effects are the same as those in embodiment 1.

What is claimed is:

1. A dental attachment comprising:

a magnetic apparatus with magnetic attractive force; and a keeper that is attracted by said magnetic apparatus, said keeper having a convex shaped part with an attractive surface, said keeper having an end face provided around and protruding from said convex shaped part, wherein said magnetic apparatus has a permanent magnet, wherein said magnetic apparatus comprises a magnetic assembly with an attractive surface and a non-magnetic guide ring made of non-magnetic material around said magnetic assembly, said non-magnetic guide ring having an end face, and wherein said non-magnetic guide ring and said attractive surface of said magnetic assembly form a concave part that receives said convex part of said keeper, said end face of said keeper facing said end face of said non-magnetic guide ring.

2. The dental attachment as set forth in claim 1, wherein at least one part of the lateral surface of said convex part of said keeper and one part of the inner lateral surface of said non-magnetic guide ring have a tapered part which can fit with each other.

3. The dental attachment as set forth in claim 1, wherein at least one part of the lateral surface of said convex part of said keeper and one part of the inner lateral surface of said non-magnetic guide ring have a straight part which can fit with each other.

4. The dental attachment as set forth in claim 1, wherein said magnetic assembly comprises:

a yoke into which said permanent magnet is inserted;

a soft magnetic shield plate comprising at least a part of said attractive surface over said permanent magnet; and a non-magnetic seal ring provided between said soft magnetic shield plate and said yoke, wherein said non-magnetic guide ring is welded to said yoke at a welded part, and wherein a distance between the welded part and said permanent magnet is at least equal to a thickness of said yoke.

5. The dental attachment as set forth in claim 1, wherein said non-magnetic guide ring and said magnetic assembly are welded to each other.

6. The dental attachment as set forth in claim 1, wherein said magnetic assembly and said non-magnetic guide ring are formed as separate components that are joined to each other.

7. A dental attachment comprising:

a keeper having a convex part; and a magnetic apparatus configured to be magnetically connected to said keeper, said magnetic apparatus comprising:

a magnetic assembly including a yoke and a permanent magnet mounted to said yoke, a guide ring made of non-magnetic material, said guide ring being joined to said yoke to form a concave part that receives said convex part of said keeper, wherein said yoke and said guide ring are formed as separate components that are joined to each other.

8. The dental attachment according to claim 7, wherein said guide ring and said yoke are formed of different materials.

9. The dental attachment according to claim 7, wherein said guide ring and said yoke are joined by welding.

10. A dental attachment comprising:

a keeper having a convex part; and a magnetic apparatus configured to be magnetically connected to said keeper, said magnetic apparatus comprising:

a magnetic assembly including a yoke and a permanent magnet mounted within a recess in said yoke, a guide ring made of non-magnetic material, said guide ring and said yoke forming a concave part that receives said convex part of said keeper, wherein said guide ring has an outer lateral surface with a concave recess.

* * * * *